United States Patent

Rapoport et al.

[19]

[11] Patent Number: 6,165,133

[45] Date of Patent: Dec. 26, 2000

[54] APPARATUS AND METHOD FOR MONITORING BREATHING PATTERNS

[75] Inventors: David M. Rapoport; Robert G. Norman, both of New York, N.Y.

[73] Assignee: New York University, New York, N.Y.

[21] Appl. No.: 09/068,799

[22] PCT Filed: Nov. 15, 1996

[86] PCT No.: PCT/US96/18619

§ 371 Date: Mar. 22, 1999

§ 102(e) Date: Mar. 22, 1999

[87] PCT Pub. No.: WO97/18752

PCT Pub. Date: May 29, 1997

Related U.S. Application Data

[60] Provisional application No. 60/006,883, Nov. 17, 1995.

[51] Int. Cl.[7] .................................................. A61B 5/08
[52] U.S. Cl. .......................................... 600/529; 600/537
[58] Field of Search ................................... 600/484, 529, 600/531, 532, 534–538

[56] References Cited

U.S. PATENT DOCUMENTS

| 4,803,997 | 2/1989 | Bowman . |
| 5,069,222 | 12/1991 | McDonald . |
| 5,190,048 | 3/1993 | Wilkinson . |
| 5,251,636 | 10/1993 | Neuman . |
| 5,513,646 | 5/1996 | Lehrman et al. ................... 600/529 |
| 5,535,739 | 7/1996 | Rapoport et al. . |
| 5,540,733 | 7/1996 | Testerman et al. . |
| 5,546,952 | 8/1996 | Erickson . |

*Primary Examiner*—Linda C. M. Dvorak
*Assistant Examiner*—Bryan K. Yarnell
*Attorney, Agent, or Firm*—Fulwider Patton Lee & Utecht, LLP

[57] ABSTRACT

A pressure sensor is combined with a temperature sensor to monitor a patient's breathing patterns. The combination of sensors enables an analysis of the patient's breathing patterns to be made without the use of a face mask even if the patient breathes through the mouth or draws only very weak breaths. The patient's sleep is therefore less likely to be disrupted by the presence of the monitoring equipment and a more accurate diagnosis of any sleep disorder can be made.

11 Claims, 5 Drawing Sheets

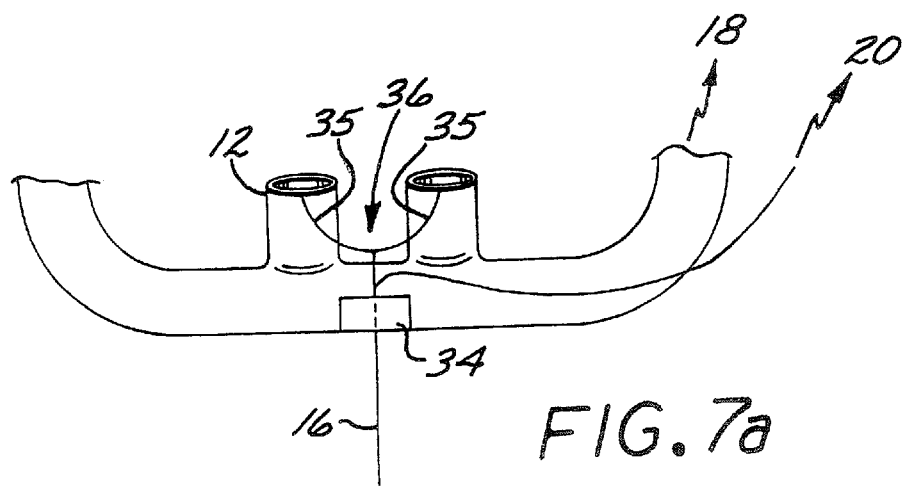
FIG. 7a
FIG. 7b
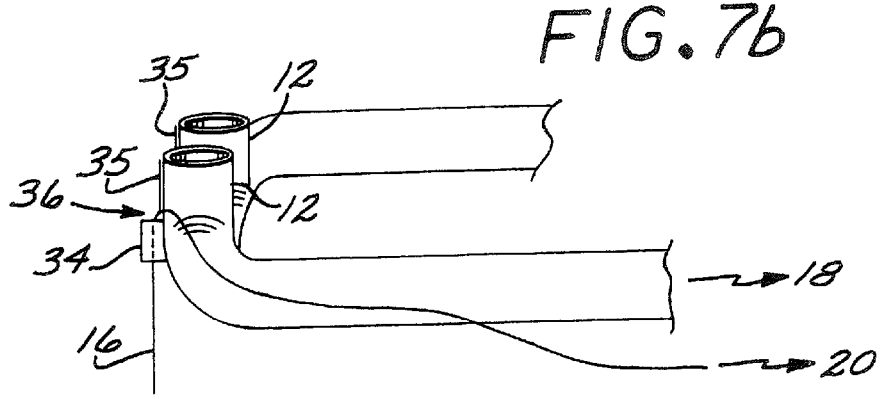
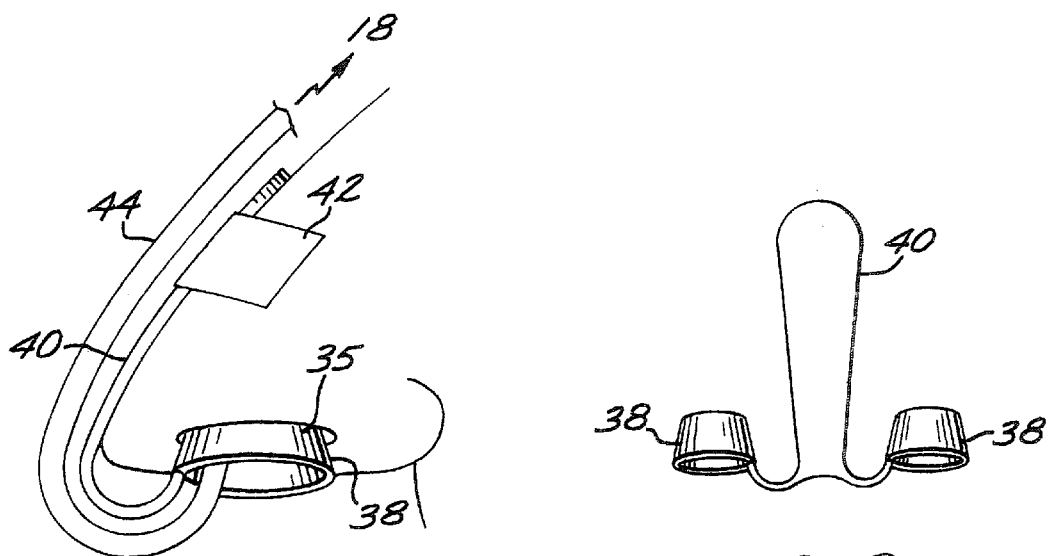
FIG. 8
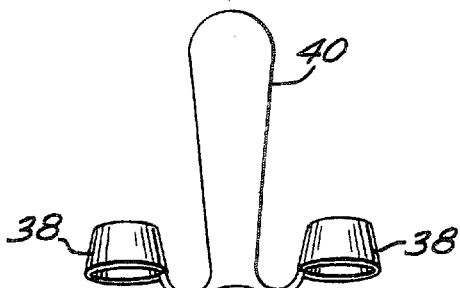
FIG. 9

APPARATUS AND METHOD FOR MONITORING BREATHING PATTERNS

This application claims the benefit of U.S. Provisional Application Ser. No. 60/006,883 filed Nov. 17, 1995.

BACKGROUND OF THE INVENTION

The present invention generally relates to the diagnosis of sleep disorders and more particularly pertains to the monitoring of a patient's breathing while asleep. Once the cause of sleep disorder has been identified, an appropriate treatment can be prescribed.

Sleep problems may have any of a number of causes including a variety of breathing disorders. For example, obstructive sleep apnea syndrome (OSAS) is a well recognized disorder which may affect as much as 1–5% of the adult population. OSAS is one of the most common causes of excessive daytime somnolence. OSAS is most frequent in obese males, and it is the single most frequent reason for referral to sleep disorder clinics.

OSAS is associated with all conditions in which there is anatomic or functional narrowing of the patient's upper airway, and is characterized by an intermittent obstruction of the upper airway occurring during sleep. The obstruction results in a spectrum of respiratory disturbances ranging from the total absence of airflow (apnea) to significant obstruction with or without reduced airflow (hypopnea and snoring), despite continued respiratory efforts. The morbidity of the syndrome arises from hypoxemia, hypercapnia, bradycardia and sleep disruption associated with the apneas and arousals from sleep.

The patholophysiology of OSAS is not fully worked out. However, it is now well recognized that obstruction of the upper airway during sleep is in part due to the collapsible behavior of the supraglottic segment during the negative intraluminal pressure generated by the inspiratory effort. Thus, the human upper airway during sleep behaves as a Starling resistor, which is defined by the property that the flow is limited to a fixed value irrespective of the driving (inspiratory) pressure. Partial or complete airway collapse can then occur associated with the loss of airway tone which is characteristic of the onset of sleep and may be exaggerated in OSAS. Central sleep apnea is associated with the failure of the body to automatically generate the neuro-muscular stimulation necessary to initiate air control a respiratory cycle at the proper time. Central sleep hypopnea has a similar cause and work associated with the use of electrical stimulation to combat the disorder is ongoing.

Detection of respiration is at the heart of physiological monitoring done during sleep. It is essential to establish that a subject is normal or to identify pauses in breathing and obstructive episodes in which abnormal airflow accounts for the arousals seen in patients with obstructive apnea, upper airway resistance syndrome, and sever snoring. The current standard form of monitoring of breathing is the thermistor or thermocouple, a temperature sensitive device placed near the nose and mouth which detects a change in temperature (hot air during exhalation, and cooler ambient air during inhalation). However, the thermistor and thermocouple devices, which lack the ability to accurately quantitate airflow once detected as they are nearly "all or none devices". Nonetheless, such devices are currently used in attempt to roughly quantify temperature changes. Other devices have been used to directly monitor airflow (pneumotachograph), but all rely on the direct capture and measurement of the volume of air passing through the nose or mouth and thus require a mask to capture the air.

More recently, it has been proposed that the contour of the airflow signal from the true flow signal (as opposed to an indirect monitor-like temperature) can be used to indicate states of abnormal upper airway patency resulting in reduced airflow (hypopnea) or elevated airway resistance with no reduction in airflow in addition to the presence of complete cessation of breathing (apnea). A technique previously proposed requires the combination of a nasal cannula with a sensitive pressure transducer. When used this way, as opposed to as a device to deliver oxygen, the interaction of the cannula tip with the human nostril creates a form of pneumotachograph head, such that the drop in pressure from inside the nose to outside (sensed by the nasal cannula) is proportional to the airflow. This signal is remarkably proportional to the signal from a calibrated pneumotachograph attached to true mask, and thus provides a very comfortable, sensitive way to monitor breathing during sleep. However, two limitations are inherent in the use of such device namely, its inability to detect mouth breathing and its poor sensitivity to very small breaths.

A more accurate approach is therefor needed that provides both a quantitative measure of airflow as well as the ability to detect mouth breathing and small breaths. Additionally, it is most desirable to provide a device with such capability that is relatively inexpensive, easy to use, and minimizes any discomfort to the patient.

SUMMARY OF THE INVENTION

The present invention overcomes the shortcomings of the prior art to provide a device and method by which a patient's breathing can accurately be monitored. The device of the invention is relatively inexpensive, is partially reusable, is easy to use, and is relatively comfortable for the patient being monitored. Once accurate data relating to a patient's breathing patterns during sleep has been gathered, a specific breathing disorder can be identified or dismissed as the cause of the patient's sleep problems and an appropriate treatment can be undertaken.

The present invention provides a device which combines a sensitive pressure transducer in communication with the patient through a nasal cannula with an appropriately positioned thermistor. The thermistor is held in place by being attached to the nasal prongs which alleviates the nuisance of having to fit and position two separate sensors to the patient. Additionally, the relatively expensive and reusable thermistor may be detachable from the relatively inexpensive and disposable cannula and nasal prong.

The outputs of the two devices are combined so as to analyze the patient's breathing patterns. As a result, the patient's breathing may be characterized as normal, subject to episodes of central or obstructive apnea or subject to episodes of central or obstructive hypopnea.

These and other features and advantages of the present invention will become apparent from the following detailed description of preferred embodiment which, taken in conjunction with the accompanying drawings, illustrate by way of example the principles of the invention.

BRIEF DESCRIPTION OF THE DRAWINGS

FIGS. 7a and 7b are front and side views of an alternative embodiment device employing a detachable thermistor configuration;

FIG. 8 is a side view illustrating a pressure sensing device in place on a patient's nose;

FIG. 9 is a front view of the device shown in FIG. 8; and

DETAILED DESCRIPTION OF THE PREFERRED EMBODIMENTS

The following embodiments provide various examples of how a pressure sensing apparatus can be combined with a temperature sensing device in accordance with the present invention. The resulting device is readily fitted to the patient and provides the data necessary to promptly diagnose a breathing disorder.

Figure 1:
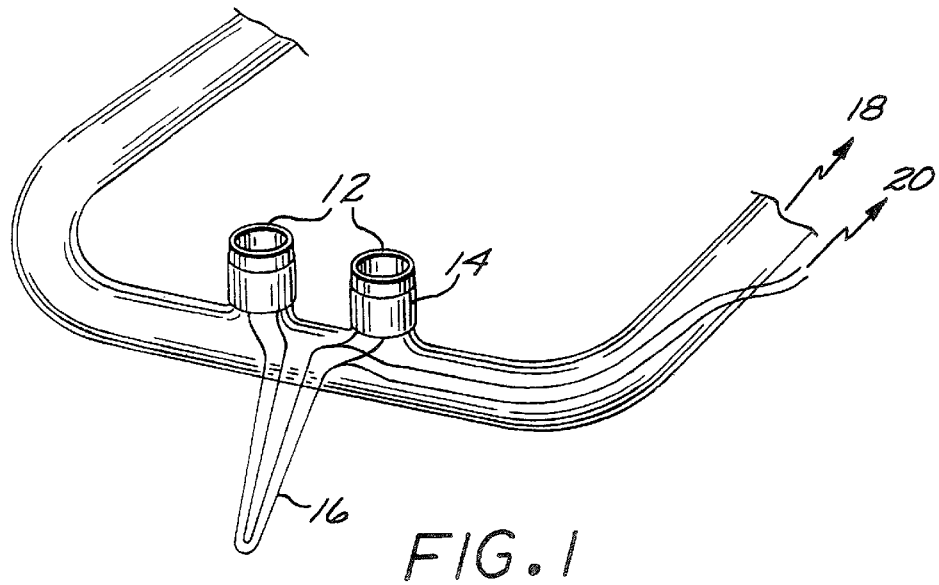
FIGS. 1–3 are perspective views of embodiments of the present invention with non-detachable thermistor configurations.

FIG. 1 illustrates a combination of nasal prongs and a heat sensor. The nasal prongs 12 extend into the patient's nostrils and are in fluid communication 18 with a sensitive pressure sensor. A thermistor is coated 14 about each nasal prong and extends downwardly 16 to cover the patient's mouth. The thermistor is electrically linked 20 with electronic sensing equipment to provide a signal that is roughly proportional to the temperature.

Figure 2:
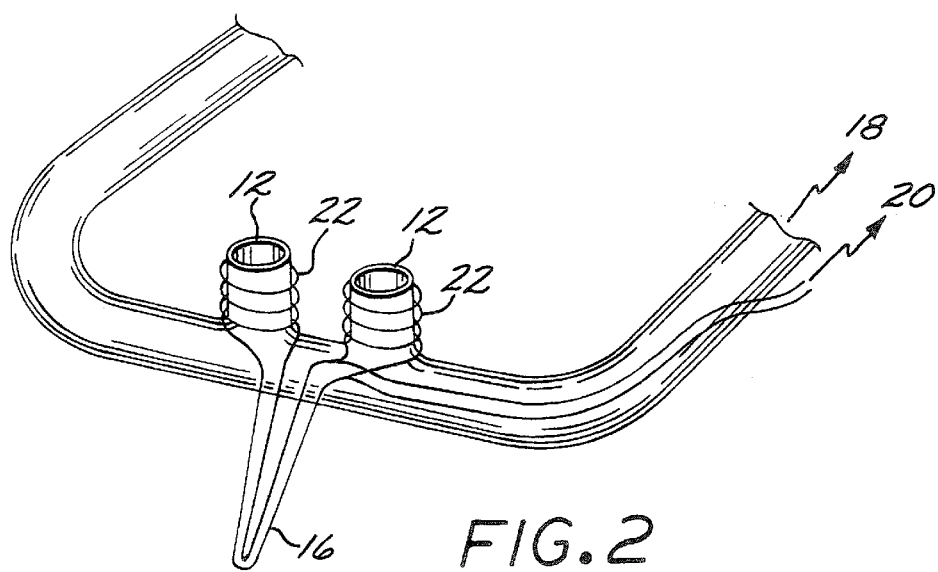

FIG. 2 illustrates an alternative embodiment wherein the thermistor 22 is wound or coiled about the nasal prongs. The thermistor additionally extends downwardly 16 over the patient's mouth.

Figure 3:
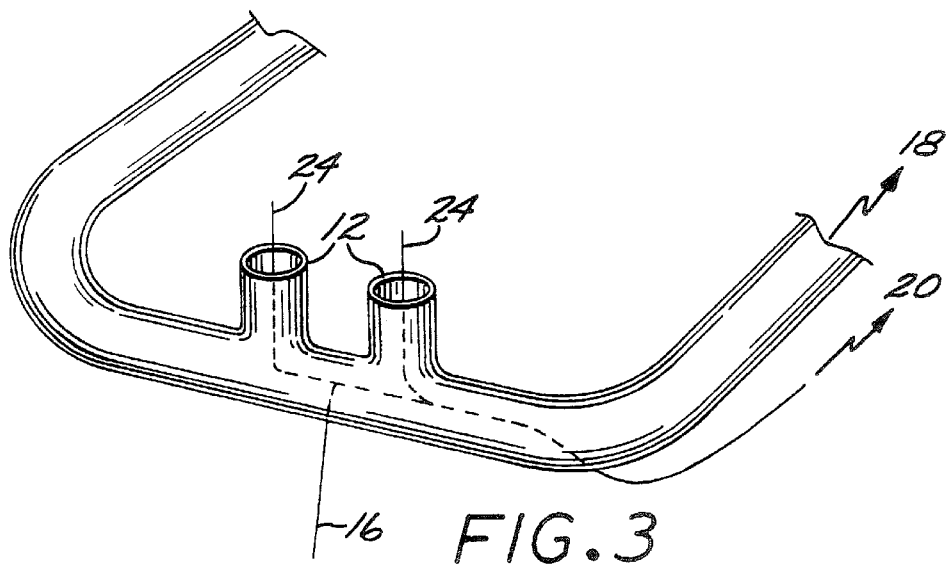

FIG. 3 provides a further alternative wherein the thermistor 24 is positioned within the cannula and extends upwardly from the nasal prongs and downwardly 16 over the patient's mouth.

Figure 4:
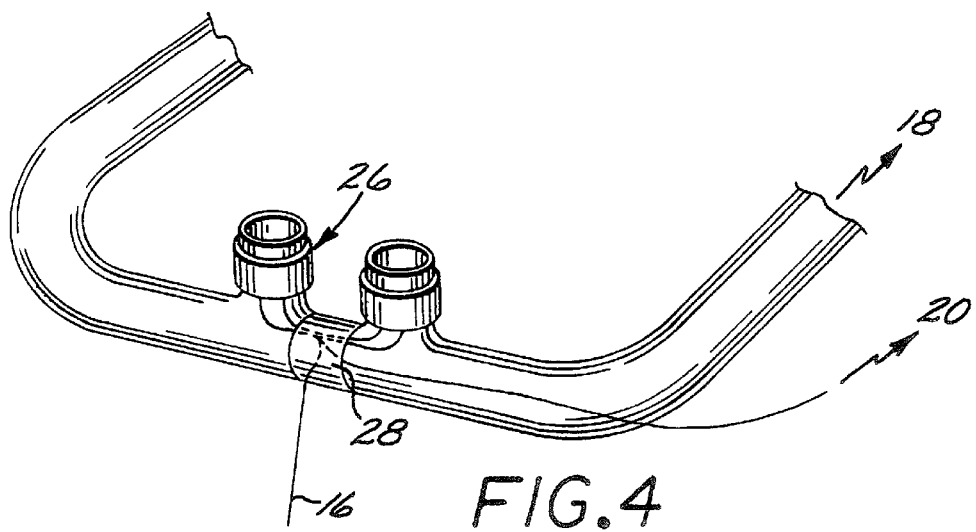
FIG. 4 is a perspective view showing a detachable thermistor element attached to nasal prongs.
Figure 5:
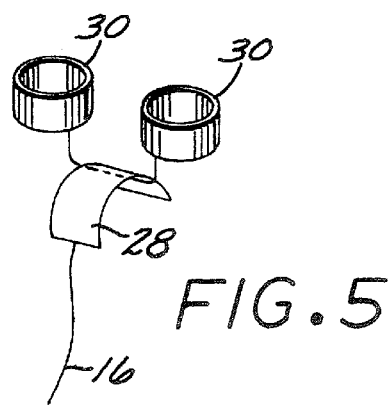
FIG. 5 is a perspective view showing a detachable thermistor element.
Figure 6:
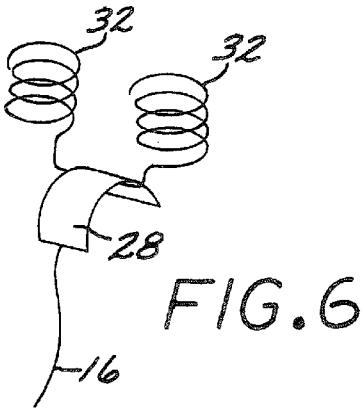
FIG. 6 is a perspective view showing another detachable thermistor element.

FIG. 4 illustrates a configuration wherein the thermistor element 26 is detachable and held in place by a clip 28. FIG. 5 shows a detachable configuration wherein the thermistor comprises bands 30 that slip over the nasal prong while FIG. 6 illustrates an embodiment wherein the thermistors comprise coils 32 that similarly fit over the nasal prongs.

FIGS. 7a and 7b illustrate an alternative embodiment of a detachable thermistor configuration wherein the nasal cannula includes an extension 34 on its front surface having a hole formed therein through which is passed the downwardly directed portion 16 of the thermistor 36. This serves to detachably hold the device in place. The upwardly directed portions 35 of the thermistor extend along the nasal prongs 12.

FIG. 8 illustrates a configuration for enhancing the sensitivity of the pressure sensor. A funnel-shaped insert 38 positioned in each nostril 35 creates a pressure drop during flow in and out of the nose. The inserts are attached to support 40 that is held against the nose 37 with tape 42 or with an adhesive backing. Conduit 44 sets the inside of the nostril in fluid communication with a pressure sensing device at 18.

FIG. 9 illustrates such embodiment in a front plane view. The device may additionally be combined with a thermistor in either a detachable or non-detachable configuration.

In operation, the nasal cannula/thermistor combination is fitted to the patient and interconnected to the pressure sensing and temperature sensing devices. As the patient sleeps, the breathing patterns are continually monitored. Analysis of the data reveals whether such breathing patterns are normal or indicative of central apnea, obstructive apnea, central hypopnea or obstructive hypopnea. In a detachable configuration, the relatively inexpensive and difficult to sterilize cannula and nasal prongs are discarded while the relatively more expensive thermistor is sterilized and reused.

Figure 10:
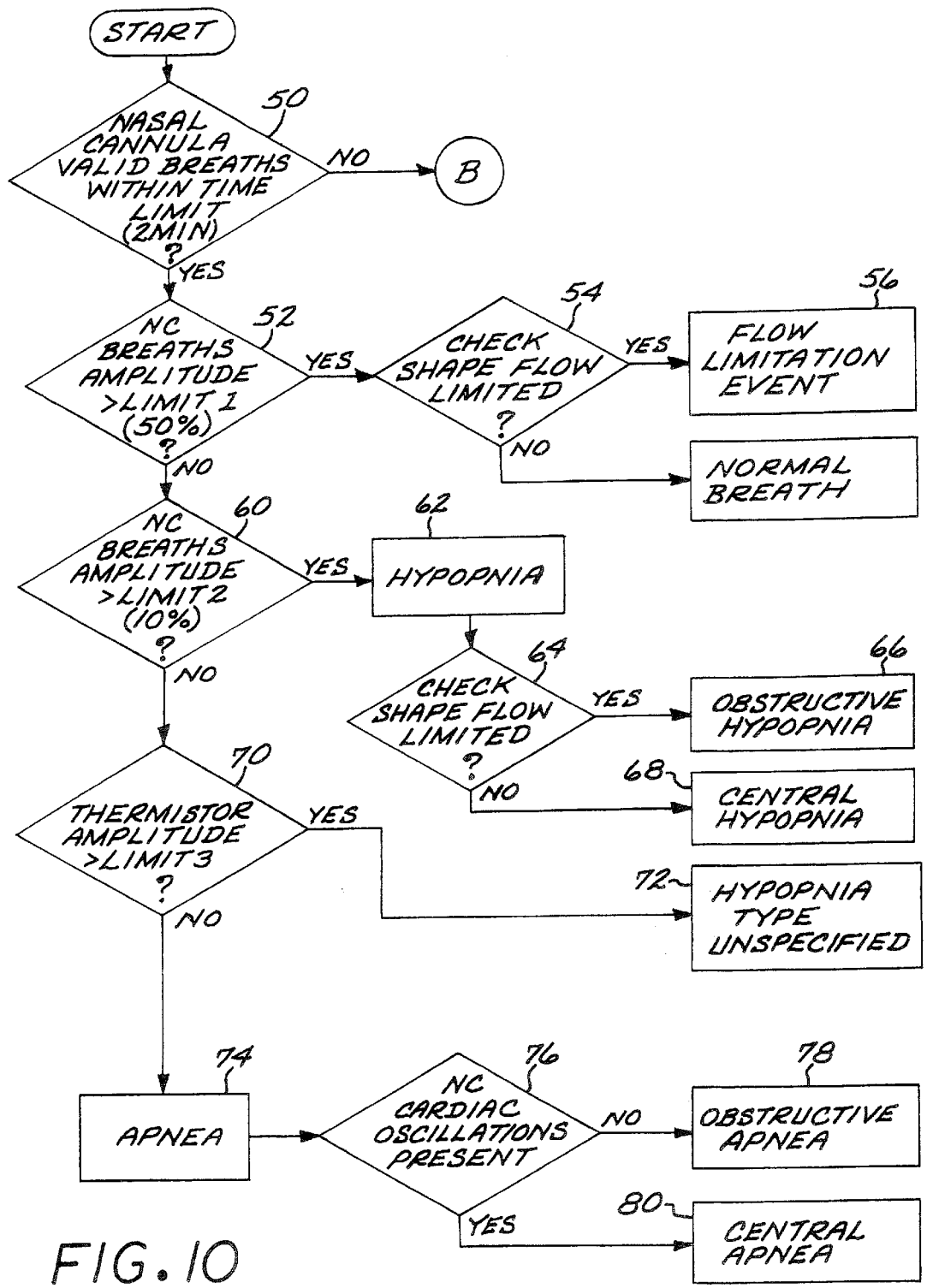
FIGS. 10 and 11 are flow charts illustrating one technique for interpreting the outputs from a pressure sensor and thermistor combination.
Figure 11:
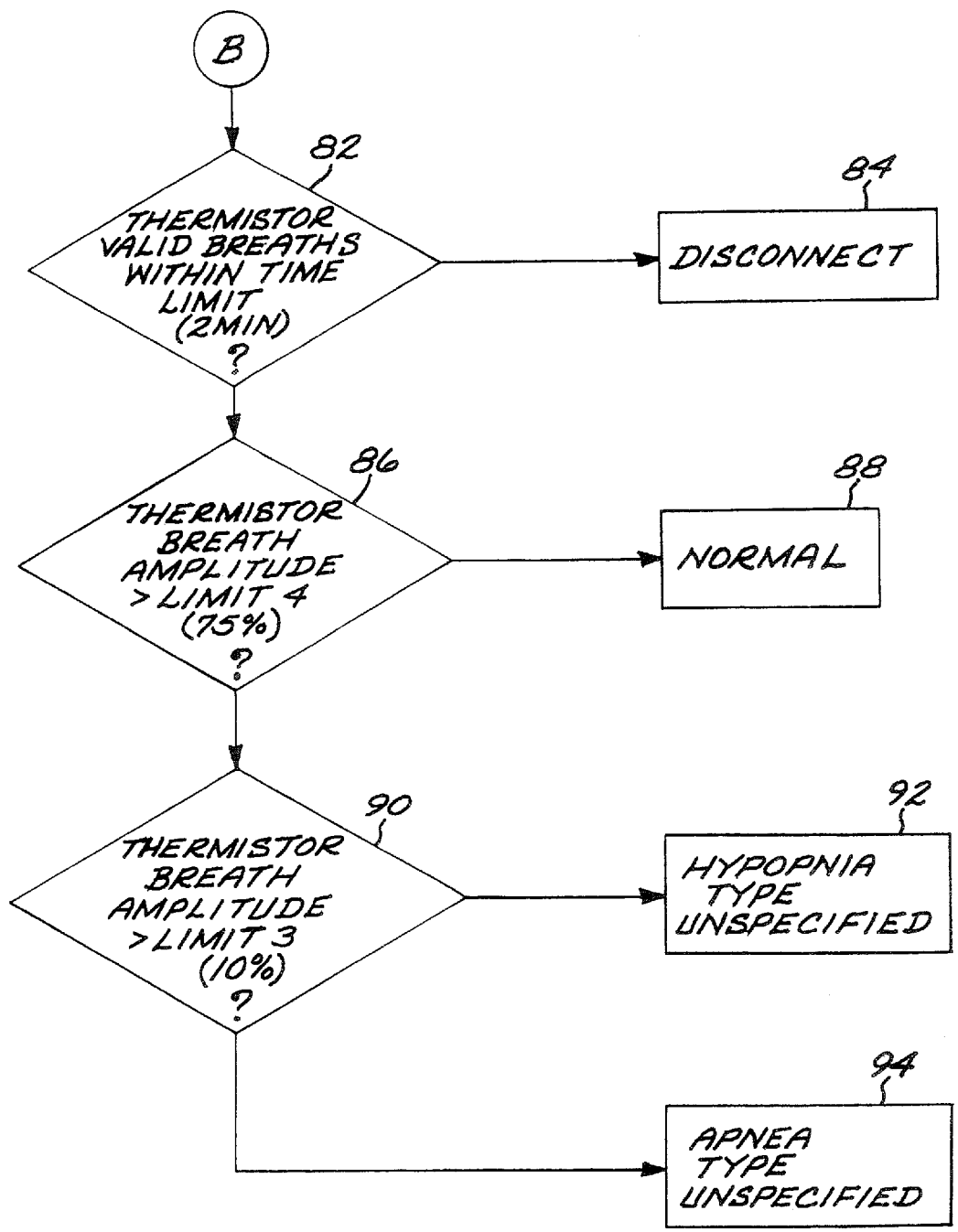

FIGS. 10 and 11 illustrate how data generated by the device of the present invention can be utilized to diagnose a breathing disorder.

As illustrated in FIG. 10, upon initiating the monitoring sequence, it is first determined at step 50 whether the pressure sensor has detected a breath within a preselected time period such as for example 2 minutes. If not, the sequence continues in FIG. 11 to rely solely on the thermistor. If a breath has been detected within the preselected time limit, the determination is made at step 52 as to whether the pressure amplitude exceeds a first preselected limit such as 50% of the average amplitude sensed in a preselected time period such as for example in the previous 5 minutes. An analysis of the pressure waveform is undertaken at step 54 wherein such analysis is now well known in the art and substantially conforms to that disclosed in U.S. Pat. No. 5,335,654 which is incorporated herein by reference. Generally, a "flow limited" shape is indicated by deviations from a substantially sinusoidal waveform, by a flattening of the curve or by the presence of plateaus in the portions of the waveform corresponding to inspiration of the patient. Even if a flow limitation event 56, is indicated, it would not amount to hypopnea by virtue of the breath amplitude that was detected. A normal appearing waveform is indicative of a normal breath 58.

If on the other hand the breath amplitude is determined to be less than the first limit at 52, it is again examined at step 60 to determine whether a second amplitude limit such as 10% is exceeded. If so, hypopnea is indicated 62 and the waveform is again checked at 64 to distinguish between obstructive and central hypopnea wherein a flow-limited shape is indicative of obstructive hypopnea. If the determination is made at step 60 that the breath amplitude is below the second amplitude limit, the thermistor amplitude is compared to a preselected limit such as 10% of the average amplitude sensed in a preselected time period such as for example in the previous 5 minutes. If such limit is exceeded, an unspecified type of hypopnea is indicated 72. If the thermistor amplitude fails to achieve the preselected limit, apnea is indicated 74 and the pressure waveform is examined for cardiac oscillation at step 76, i.e. regular, small-amplitude flow pulsations with a frequency in the range of the cardiac frequency. These pulsations can be detected from the flow signal after it is appropriately filtered and transformed to magnify their amplitude. The signal transformation function (which preferentially magnifies the amplitude of the signal near its average value) may include, but not be limited to, nonlinear mathematical functions (e.g. square root) and look-up tables. These periodic fluctuations are then detected in the transformed signal with valiance and/or period amplitude techniques which identify fluctuations at a frequency similar to that of a cardiac cycle (e.g. 40–120/min). If such oscillations are not present, obstructive apnea is indicated 78, if on the other hand such oscillations are identified, central apnea is indicated 80.

Returning to step 50, if an initial determination had been made that no breaths had been detected by the pressure sensor during the preselected time period, the output of the thermistor is checked at step 82 to determine whereby any breaths had been detected thereby during a preselected time interval of for example 2 minutes. If no thermistor activity had registered, a disconnect is indicated 84 and alarm may be sounded. If some thermistor activity is noted at 82, its amplitude is checked at step 86. An amplitude greater than a preselected limit is indicative of normal breathing 88 albeit through the mouth. Failure to attain such limit causes the amplitude to be compared to a significantly lower limit at step 90. An amplitude greater than such limit is indicative of an unspecified type of hypopnea at 92 while an amplitude less than such limit is indicative of an unspecified type of apnea. The absence of pressure signal precludes analysis of its waveform in an effort to distinguish between obstructive or central forms of hypopnea or apnea.

In sum, the highly accurate pressure signal is initially relied upon in an effort to diagnose a breathing disorder. In the absence of a strong pressure signal, the less accurate temperature signal is resorted to for the purpose of analysis. The combination of the two signals provides a much more accurate indication of a patient's breathing performance than could be provided by the exclusive reliance on either signal.

Such monitoring is continued for any desired period of time. The types of occurances and the frequency of such occurances of abnormal breathing are subsequently analyzed to render an opinion as to whether a breathing disorder is indicated which in turn provides insight into any sleep disorder.

While a particular form of the invention has been illustrated and described, it will also be apparent to those skilled in the art that various modifications can be made without departing from the spirit and scope of the invention. More particularly, a variety of different temperature sensors may be employed, and such sensors can be combined with the nasal cannula and prongs in any of a variety of ways so as to ensure proper positioning and optionally provide for detachability. In analyzing the data generated by the combination of pressure sensor and temperature sensor, different limits may be set than were described in the preferred embodiment. Accordingly, it is not intended that the invention be limited except by the appended claims.

What is claimed is:

1. A breath monitoring device, comprising:
   a pressure transducer adapted to be in fluid communication with said patient's nose, operative to generate a signal indicative of air pressure therein;
   a temperature sensor operative to generate a signal indicative of temperature in said patient's nose and adjacent said patient's mouth; and
   a signal processor for simultaneously evaluating said pressure signal and said temperature signal to facilitate the analysis of said patient's breathing patterns for hypopnea and apnea.

2. The monitoring device of claim 1, wherein said pressure transducer is adapted to be in fluid communication with said patient's nose via a nasal cannula and nasal prongs.

3. The monitoring device of claim 2, wherein said temperature sensor is attached to said nasal prongs.

4. The monitoring device of claim 3, wherein said temperature sensor is detachable from said nasal prongs.

5. The monitoring device of claim 1, wherein said temperature sensor comprises a thermistor.

6. The monitoring device of claim 1, wherein said signal processor is capable of analyzing the waveform of said pressure signal to determine whether an obstruction is indicated.

7. The monitoring device of claim 6, wherein said signal processor is capable of analyzing the waveform of said pressure signal to identify cardiac oscillations.

8. The monitoring device of claim 1, wherein said signal processor is capable of analyzing the waveform of said pressure signal to identify cardiac oscillations.

9. A method for analyzing a patient's breathing patterns, comprising the steps of:
   sensing pressure within said patient's nose;
   sensing temperature within said patient's nose and adjacent said patient's mouth;
   determining whether a sufficiently strong pressure signal is present in order to analyze the patient's breathing; and
   defaulting to an analysis of the temperature signal in the event a weak or no pressure signal is detected.

10. The method of claim 9 further comprising the step of:
    determining whether the sufficiently strong pressure signal has a waveform indicative of an obstruction.

11. The method of claim 9 further comprising the steps of:
    examining whether the sufficiently strong pressure signal includes cardiac oscillations.

* * * * *